United States Patent [19]

Walker, Jr.

[11] 4,226,240
[45] Oct. 7, 1980

[54] SURGICAL FORECEPS

[76] Inventor: William E. Walker, Jr., 9th St. & Sugar Estate Rd., St. Thomas, V.I. 00801

[21] Appl. No.: 43,796

[22] Filed: May 30, 1979

Related U.S. Application Data

[63] Continuation-in-part of Ser. No. 831,221, Sep. 7, 1977, abandoned, which is a continuation-in-part of Ser. No. 706,847, Jul. 19, 1976, abandoned.

[51] Int. Cl.³ .............................................. A61B 17/28
[52] U.S. Cl. .................................................... 128/321
[58] Field of Search .............. 128/321, 322, 325, 340, 128/346, 335, 335.5

[56] References Cited

U.S. PATENT DOCUMENTS

| | | | |
|---|---|---|---|
| 1,852,542 | 4/1932 | Sovatkin | 128/321 X |
| 2,618,268 | 11/1952 | English | 128/321 |
| 2,842,132 | 7/1958 | Soltero et al. | 128/322 |
| 2,887,111 | 5/1959 | Diaz | 128/321 |

FOREIGN PATENT DOCUMENTS

| | | | |
|---|---|---|---|
| 20743 | 7/1905 | Fed. Rep. of Germany | 128/321 |
| 524920 | 4/1931 | Fed. Rep. of Germany | 128/325 |
| 378427 | 10/1907 | France | 128/321 |

OTHER PUBLICATIONS

Abreu et al., "New Forceps for Petropubic Prostatectomy", Jour. of Urology, 107:626, Apr. 1972.
Codman General Surgical Instruments, p. 168, (1973).
*Sklar* Gynecological and Obstetrical Instruments.
McElmoyle, W. A., "Two New Gastrectomy Clamps", *Lancet*, 265, 6778, 169, (1953).
Ross, H. I., "An Intestinal Holding Clamp for Deep Pelvic Anastomosis of the Colon", Surg., Gyn. & Obs. 97²:248–249, 1953.

*Primary Examiner*—Robert W. Michell
*Assistant Examiner*—Michael H. Thaler

[57] ABSTRACT

Surgical forceps comprising cross members having a pair of gripping arms pivotally connected to a pair of clamping arms comprising a pair of end members directed away from the axis of the gripping arms and terminating with a pair of slightly curved mating jaws having aligned notches disposed on their outer surfaces to accommodate a needle for sutures. The pair of mated jaws are disposed in a plane substantially perpendicular to the plane containing the pair of end members.

17 Claims, 6 Drawing Figures

U.S. Patent  Oct. 7, 1980  4,226,240
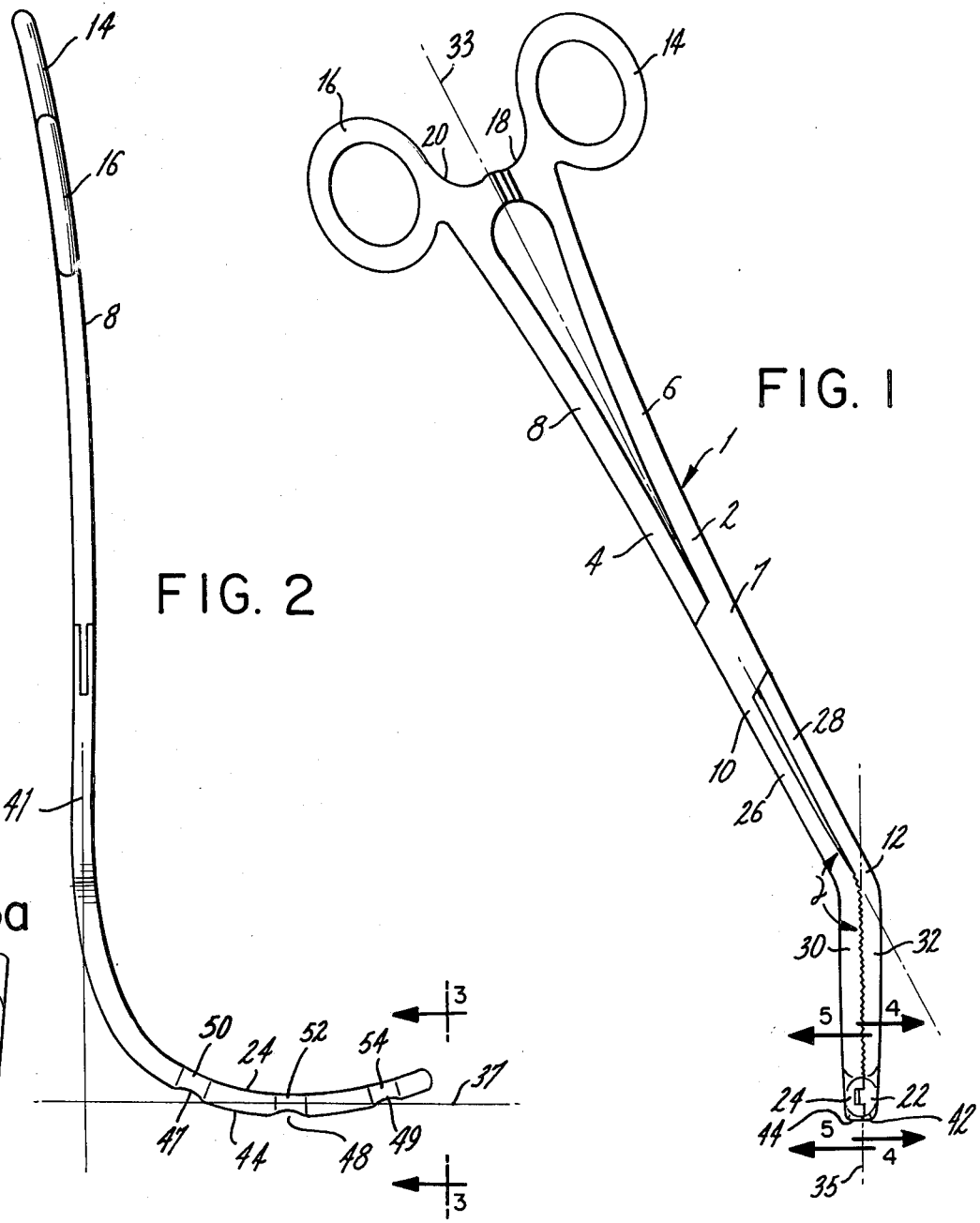
FIG. 1
FIG. 2
FIG. 3a
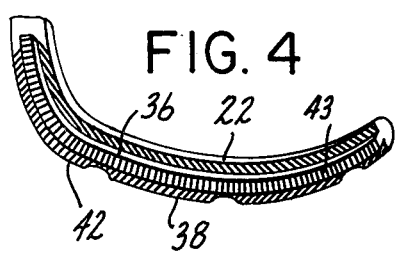
FIG. 4
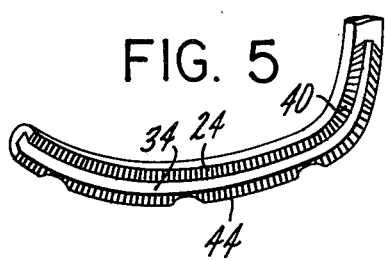
FIG. 5
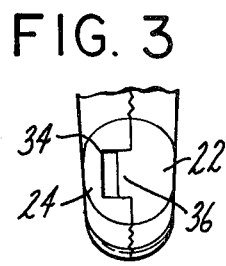
FIG. 3

SURGICAL FORECEPS

This application is a continuation-in-part application of Ser. No. 831,221 filed Sept. 7, 1877, now abandoned which in turn is a continuation-in-part of Ser. No. 706,847 filed July 19, 1976, now abandoned.

FIELD OF THE INVENTION

This invention relates to a surgical forceps and specifically to a manual vaginotomy clamp for use in surgical operations and specifically abdominal hysterectomy to more effectively separate and extirpate the uterus from the vagina.

BACKGROUND OF THE INVENTION

In the surgical procedure known as abdominal hysterectomy, the uterus is extirpated from the vagina at the junction of the two elements. This entails the partial clamping of the junction of the uterus and the vagina and then the excising of the uterus in a simple cutting operation or performing a plurality of cutting steps until the uterus is completely severed. Usually these operations involve inexact severing of the uterus which leaves a ragged edge, i.e., redundant tissue on the vaginal cuff. Despite the use of conventional clamps affixed on the edges of the vagina, the vaginal cuff is quite vascular and generally results in moderately profuse bleeding from the ragged edges, especially at the lateral angles of the vagina. The combination of the ragged edges of the vaginal cuff and tendency towards bleeding can result in the direct contamination of the vaginal cuff with vaginal bacterial flora, thus possibly resulting in the following major post-operative problems:

1. The infection and abscess of the vaginal cuff, and
2. Hemorrhage from the vaginal cuff usually within eight to fourteen days after the surgical operation.

Another drawback with using conventional type clamping means is that the inexact severing of the uterus could result in the removal of too little or too much of the vaginal edges anteriorly or posteriorly. This possibly could occur due to slipping of portions of the vaginal cuff (tissue) from the conventional type surgical forceps being employed.

U.S. Pat. No. 2,887,111 discloses a surgical forceps having uneven jaws so that one of the jaws extends with a projection which possesses an eye as in a sewing needle through which an appropriate thread may be passed for the tieing or binding of veins or the like.

U.S. Pat. No. 2,842,132 discloses a surgical clamp having relatively thin jaw sections with teeth therein for gripping a relatively small blood vessel longitudinally thereof. The jaw sections of the surgical clamp have interlocking fixation means to prevent scissoring or shifting of the jaw sections relative to each other while applying clamping pressure to the jaw sections for bringing the walls of a portion of a blood vessel into contact with each other.

U.S. Pat. No. 1,852,542 discloses a scissor-type surgical clamp having a mortise joint between the crossing portions of the clamp and having means for adjusting the clamp to tighten or loosen the connection between the crossed portions so that true alignment between the jaws or working points of the instrument may be effectively maintained.

French Pat No. 378,427 discloses a scissor-type surgical clamp having affixed to pivoted means a pair of extended curved members disposed in a plane containing a pair of gripping members extending in the opposite direction from the securing means. The curved members have spaced-apart edge slots which can be used to accommodate a needle for sutures.

In an article titled "New Forceps For Retropubic Prostatectomy" appearing in the Journal of Urology, 107:626, April 1972, a forceps is disclosed in which one of its extended jaws has four keyholes to receive sutures.

It is an object of the present invention to provide forceps for use in surgical operations which has hemostastosis means and appropriately spaced-apart grooves or notches for accommodating a needle for sutures.

Another object of the present invention is to provide surgical forceps having extended jaws which substantially conform to the anatomical curve of the cervix.

Another object of the present invention is to provide surgical forceps having a pair of extended jaws adapted to provide a crushing action so as to instantly provide hemostasis through the entire width of the body organ contained within the jaws.

Another object of the present invention is to provide surgical forceps that can be used in place of a plurality of conventional clamps presently being employed in certain surgical operations, such as abdominal hysterectomy.

Another object of the present invention is to provide surgical forceps that will expedite and shorten the surgical time required for abdominal hysterectomy.

Another object of the present invention is to provide surgical forceps which comprise few and simple parts and which will be easy to manipulate for use in surgical operations.

Another object of the present invention is that in cancer surgery two of the forceps can be employed with the first being used to effectively seal off the uterus cavity from possibly bleeding of the cancer cells into the vagina and abdominal cavity and the second being used to lift and remove the extirpated cancer-containing uterus out of the abdominal cavity.

The foregoing and additional objects will become more fully apparent from the following description and the accompanying drawings.

SUMMARY OF THE INVENTION

The invention relates to a surgical forceps comprising a pair of cross members having securing means for pivotally securing the members to one another, said cross members having a first set of arms extending in a first direction from the securing means and a second set of arms secured to said first set of arms and extending in an opposite direction from said securing means, said first set of arms adapted with gripping means for pivoting said first set of arms and said second set of arms about the securing means; the second set of arms having a pair of end members substantially disposed in a plane containing the first set of arms and directed away from the longitudinal axis of the first set of arms, and the extremity of the end members terminating with a set of mating jaws disposed in a plane substantially perpendicular to the plane containing the securing means, said set of jaws comprising a first jaw having spaced-apart notches disposed in its outer lengthwise edge and a second jaw having a like number of notches disposed in its outer lengthwise edge such that when the jaws are in a closed mated position, the notches are in alignment.

The pair of end members of the second set of arms could have an arcuate configuration; be composed of straight segments sequentially inclined so as to provide a somewhat overall curved configuration; be composed of a first straight segment terminating in a curved or arcuate segment; be composed of a straight segment in alignment with the longitudinal axis of the first set of arms and a second straight segment disposed at an angle other than 0° with the longitudinal axis of the first set of arms. The longitudinal axis of the end segment of the end members should form an angle of between about 90° and 150°, preferably between about 110° and 130°, and most preferably about 120° with the longitudinal axis of the first set of arms. This will insure that the first set of arms containing the gripping means will not unnecessarily obstruct the line of view of the physician to the body organ clamped between the jaws and also permit the physician to effectively maneuver the forceps during the operation so as to facilitate the clamping and extirpation of the vaginal cuff.

Preferably, the inner surface of the first jaw should have a lengthwise groove, the inner surface of the second jaw should have a lengthwise projection and said projection should be shaped to mate with and seat within the groove in the inner surface of the first jaw in a tongue and groove manner. The projection and groove can have any polygonal configuration as long as the projection mates with and seats within the groove. This tongue and groove arrangement will provide a lengthwise crushing action on the body organ contained within the jaws and thereby effect hemostasis through the entire length of the organ within said jaws and also prevent slipping of the organ from the forceps.

In addition, the mating surfaces of the jaws of the surgical forceps could be serrated, i.e., a formation resembling the toothed edge of a saw and disposed such that when the forceps are in the closed position, the toothed edge surface of one jaw will mate within the toothed edge surface of the other jaw. The serration can be extended substantially across the width of the jaws or extended lengthwise of the jaws. Thus when the forceps are pivoted toward the closed position, the serrated surfaces will help to provide an additional crushing action on the body organ contained therebetween which will further effect hemostasis through the entire width of the organ within the jaws and also prevent slipping of the organ from the forceps.

The extended jaws may be appropriately curved to conform to the anatomical curve of the cervix so that when the forceps are used, an almost instant hemostasis can be provided through the entire width and length of the vaginal cuff with a simple crushing action imparted through a closing of the forceps while simultaneously preventing slipping of the vaginal cuff from the forceps.

The outer lengthwise edge of each of the jaws has notches, e.g., expanded U-shaped, that are sufficiently spaced apart so that sutures can be placed in a body organ held between the jaws. When the surgical forceps are for use in abdominal hysterectomy operations, the center point of the notches which are disposed on the outer curved edge of the jaws, i.e., the edge facing away from the gripping means, can be spaced apart between about ⅜ and about ¾ inch, preferably about 9/16 inch. For abdominal hysterectomy applications, three spaced-apart notches will generally be sufficient for effective suturing of the vagina. The areas of the outer side surface of the jaws disposed adjacent to and substantially perpendicular to each of the notches could be burnished or dull finished, or slightly indented, so as to highlight the location of the notches and thereby aid the surgeon in finding the suture notches during an operation.

The present invention will become apparent from the following description thereof when considered together with the accompanying drawings which are set forth as being exemplary of embodiments of the present invention and are not intended, in any way, to be limitative thereof and wherein:

FIG. 1 is a front view of the surgical forceps of this invention.

FIG. 2 is a side view of the surgical forceps as shown in FIG. 1.

FIG. 3 is an enlarged front view of the mating jaws of the surgical forceps as shown in FIG. 2 from line 3—3.

FIG. 3a is another embodiment of an enlarged front view of the mating jaws for use in the surgical forceps of this invention.

FIG. 4 is an inner side view of one of the jaws of the surgical forceps as shown in FIG. 1 through line 4—4.

FIG. 5 is an inner side view of the other jaws of the surgical forceps as shown in FIG. 1 through line 5—5.

Referring in detail to FIGS. 1 and 2, there is shown surgical forceps 1 comprising a pair of cross members 2, 4 pivoted to one another by pivotal connection 7 such as with a box or mortise type joint. Each of the cross members 2, 4 comprise arms 6 and 8, respectively, extending from the pivotal connection means 7 in one direction and arms 10 and 12, respectively, extending from the pivotal connection means 7 in an opposite direction. Arms 6 and 8 terminate with looped handle portions 14 and 16, respectively, for receiving a user's fingers for pivoting arms 6 and 8 about pivotal connection 7. As shown in FIGS. 1 and 2, the pivotal connection 7 is located at the rearward portion of arms 6 and 8 so as to substantially be in the plane therewith. As stated above, arms 6 and 8 have looped handle portions 14 and 16, respectively, so that the user can operate the forceps in a conventional manner, and as in all instruments of this type, the arms possess catches 18 and 20, respectively, forming a broach for maintaining the corceps in a closed position after crushing a part of an organ between jaws 22 and 24 as discussed hereinafter.

A first pair of straight segments 26, 28 of arms 10 and 12 extend from pivotal connection 7 and then culminate in a second pair of segments 30, 32. The angle formed between the longitudinal axis 33 of the first set of arms and the longitudinal axis 35 of the segments 30, 32 forms an angle $\alpha$ which is shown to be about 120°. As stated above, angle $\alpha$ could vary, for example, from between about 90° to 150°, preferably between about 110° and 130° and most preferably about 120°. The extremity of segments 30, 32 terminate with slightly curved or arcuate mating jaws 24 and 22, respectively, which lie in a plane 37 substantially perpendicular to the plane 41 containing pivotal connection 7 as shown by FIGS. 1 and 2. Plane 37 is defined as the plane containing the longitudinal axis that bisects the side area 52 disposed adjacent to and substantially perpendicular to the center outer edge notch 48 as shown in FIG. 2. If an even number of notches are employed, then the plane 37 would be defined as a plane containing a line that contains the center point of the two side areas disposed adjacent to and substantially perpendicular to the two center outer edge notches. The jaws 22 and 24 are shown curved to the anatomical curve of the cervix.

As shown in FIGS. 3 and 5, jaw 24 has a lengthwise or longitudinal groove 34 and as shown in FIGS. 3 and 4, jaw 22 has a lengthwise or longitudinal projection 36.

As shown in FIG. 3, the longitudinal projection 36 of jaw 22 is designed to mate within the longitudinal groove 34 of jaw 24. The top surface of projection 36 has serrations 43. As stated above, this arrangement will provide a crushing action on the body organ contained within the jaws 22, 24 and thereby effect hemostasis through the entire length of the organ within said jaws while also preventing slipping of the organ.

As shown in FIGS. 4 and 5, the mating jaws 22, 24 have widthwise serrations 38 and 40, respectively. Thus when the arms 6 and 8 are pivoted to the closed position, the jaws 22 and 24 are brought into a mating position which will be sufficient to widthwise crush and thereby provide an almost instant hemostasis through the width of the body organ clamped therebetween while simultaneously preventing slipping of the organ through the forceps.

FIG. 3a shows an enlarged front view of another embodiment of mating jaws 21 and 23 for use in this invention. Specifically, the only difference between the jaws 21 and 23 of this view and the jaws 22 and 24 of FIG. 3 is that the projection 46 on jaw 23 has a truncated pyramidal shape while projection 36 on jaw 22 has a rectangular shape. Thus in accordance with this invention, the projection could have any polygonal configuration. The only requirement is that the groove in the mating jaw be shaped in a similar manner so that the projection can seat and mate within the groove.

As shown in FIGS. 1 and 2, the outer edges 42 and 44 of jaws 22 and 24, respectively, have three spaced-apart notches 47, 48 and 49. In the closed position, notches 47, 48 and 49 in jaw 22 will be in alignment with notches 47, 48 and 49 in jaw 24 so as to provide slots to accommodate a needle for suturing a body organ confined and secured between the jaws. As shown in FIGS. 1 and 2, the user, such as a surgeon, can grasp the forceps by the looped members and by conventional pivoting can open and close the jaws of the forceps. By having the jaws of the forceps oriented approximately 90° to the gripping arm members and having the second pair of segments 30 and 32 disposed at an angle between about 90° to 150°, most preferably 120°, from the first pair of segments 26 and 28, the user can squeeze a body organ between the jaws thereby exposing the squeezed area without having the gripping arm obscuring or blocking the view and access to said squeezed area. To aid the surgeon locating the suture notches 47, 48 and 49, the areas designated 50, 52 and 54, respectively, adjacent the notches are shown slightly indented. The length of each of the areas 50, 52 and 54 is approximately equal to the length of the respective notches 47, 48 and 49 as shown in FIG. 2.

When using the surgical forceps of this invention in an abdominal hysterectomy operation, the forceps clamp the uterus at its cervical end and squeeze it down so as to force the lower aspect of the uterus (hereinafter referred to as cervix) cephalad or upwards. Three sutures are then placed through the notches in the jaws of the forceps to secure the vaginal cuff. The cervis uteri can then be excised in one step without leaving redundant or uneven vaginal edges at the vaginal junction. The surgical forceps of this invention serve to provide excellent hemostasis by its crushing action of the vaginal cuff secured between the jaws of the forceps and also provide a seal against vaginal contamination as it effectively closes off the entire vagina. The use of the surgical forceps as a single clamp during the operation will not obscure the area of the uterus being excised.

The surgical forceps of this invention can effectively shorten the time of excising the cervis uteri from the vagina from 15 to 30 minutes. This reduction in operating time can materially benefit the patient by shortening anesthetic time which can be most important in the marginally healthy patient who requires abdominal hysterectomy.

It is to be understood that other modifications and changes to to the preferred embodiment of the invention herein shown and described can also be made without departing from the spirit and scope of the invention.

What is claimed is:

1. A surgical forceps comprising a pair of cross members having securing means for pivotally securing the members to one another, said cross members having a first set of arms extending in a first direction from the securing means and a second set of arms secured to said first set of arms and extending in an opposite direction from said securing means, said first set of arms adapted with gripping means for pivoting said first set of arms and said second set of arms about the securing means; the second set of arms comprising a pair of end members substantially disposed in a plane containing the first set of arms and directed away from the longitudinal axis of the first set of arms, and the extremity of the end members terminating with a set of mating jaws disposed in a plane substantially perpendicular to the plane containing the securing means, said set of jaws comprising a first jaw having spaced-apart notches disposed in its outer lengthwise edge and a second jaw having a like number of notches disposed in its outer lengthwise edge such that when the jaws are in a closed mated position, the notches are in abutting alignment.

2. The surgical forceps of claim 1 wherein one of the jaws has a longitudinal groove in its inner surface and the other jaw has a longitudinal projection on its inner surface, said groove and said projection being designed such that when the jaws are in the mated closed position, the projection will mate with and seat within the groove.

3. The surgical forceps of claim 2 wherein the projection and groove has a polygonal configuration.

4. The surgical forceps of claim 2 wherein the projection and groove have a substantially rectangular shaped configuration.

5. The surgical forceps of claim 4 wherein the inner surface of the projection is serrated.

6. The surgical forceps of claim 1 wherein the longitudinal axis of the first set of arms forms an angle of between about 90° and 150° with the longitudinal axis of the end members.

7. The surgical forceps of claim 6 wherein the angle is between about 110° and 130°.

8. The surgical forceps of claim 7 wherein the angle is about 120°.

9. The surgical forceps of claim 1 wherein the second set of arms comprises a first pair of segments substantially in axial alignment with the first set of arms and extending with a second pair of segments directed away from the longitudinal axis of the first set of arms.

10. The surgical forceps of claim 9 wherein the longitudinal axis of the first set of arms forms an angle of between about 90° and about 150° with the longitudinal axis of the second pair of segments.

11. The surgical forceps of claim 10 wherein the angle is between about 110° and 130°.

12. The surgical forceps of claim 11 wherein the angle is about 120°.

13. The surgical forceps of claim 1 wherein the jaws are arcuately shaped.

14. The surgical forceps of claim 1 wherein the inner surface of each jaw is serrated.

15. The surfical forceps of claim 14 wherein the serrations are oriented widthwise on the inner surface of each jaw.

16. The surgical forceps of claim 1 wherein the outer edge of the extending jaws has three spaced-apart notches.

17. The surgical forceps of claim 16 wherein the center point of each notch is spaced apart from the center point of an adjacent notch by between about $\frac{3}{8}$ and about $\frac{3}{4}$ inch.

* * * * *